(12) United States Patent
Vu et al.

(10) Patent No.: US 10,863,767 B2
(45) Date of Patent: Dec. 15, 2020

(54) DEVICE FOR DELIVERY OF SMOKABLE CANNABIS AND MANUFACTURING METHOD FOR SAME

(71) Applicant: CMG Partners, Inc., San Jose, CA (US)

(72) Inventors: Michael Viet Thang Vu, San Jose, CA (US); Sarah Rose Rothrock, San Francisco, CA (US); Michael William Bell, Sunnyvale, CA (US); Nelson Miguel Ricardo Martinez, Santa Clara, CA (US); Aaron Levy, San Jose, CA (US); Steven Stubblefield, Encinitas, CA (US)

(73) Assignee: CMG Partners, Inc., San Jose, CA (US)

( * ) Notice: Subject to any disclaimer, the term of this patent is extended or adjusted under 35 U.S.C. 154(b) by 33 days.

(21) Appl. No.: 15/616,802

(22) Filed: Jun. 7, 2017

(65) Prior Publication Data

US 2018/0352849 A1   Dec. 13, 2018

(51) Int. Cl.
*A24C 5/02* (2006.01)
*A24B 3/08* (2006.01)
(Continued)

(52) U.S. Cl.
CPC ............... *A24C 5/02* (2013.01); *A24B 3/08* (2013.01); *A24B 7/00* (2013.01); *A24B 15/16* (2013.01); *A61K 36/185* (2013.01)

(58) Field of Classification Search
None
See application file for complete search history.

(56) References Cited

U.S. PATENT DOCUMENTS 3,911,933 A * 10/1975 Crisp .................. A24C 5/44
                                                                131/47
8,393,563 B2 * 3/2013 Chaoui ................. B02C 18/08
                                                                241/168

(Continued)

FOREIGN PATENT DOCUMENTS

WO    2008150130 A1    12/2008
WO    2016019353 A1    2/2016

OTHER PUBLICATIONS

Old Hippie, "The Secret of Old Hippie's Special Blend of Marijuana Strains", Jan. 27, 2012, Beyond Chronic, accessed Nov. 9, 2017 http://beyondchronic.com/2012/01/secret-old-hippie-blend-marijuana-strains/.*

(Continued)

*Primary Examiner* — Michael J Felton
(74) *Attorney, Agent, or Firm* — Brian R. Galvin; Galvin Patent Law LLC

(57) ABSTRACT

A delivery device for smokable cannabis and a manufacturing method for same with a defined active cannabis compound. Plant material from a plurality of cannabis plants representing a plurality of cannabis cultivars is harvested based on parent cultivars' active cannabis compound profile. Plant material is shredded to a size range applicable to loading into a smokable device, measured proportions of plant materials are combined to produce a mixed batch with a projected desirable active cannabis compound profile. Material is then processed, analyzed, loaded into smokable delivery device, labeled and distributed.

4 Claims, 4 Drawing Sheets

| Strain 310 | THC 311 | CBD 312 | Terpenoids 313 | v 314 |
|---|---|---|---|---|
| A 315 | 17±4% 331 | 0.2±0.05% 336 | 0.5±0.3% 341 | v.1 |
| B 316 | 19-26% 332 | 0-0.3% 337 | 0.15-3.0% 342 | v.2 |
| C 317 | 4-7% 333 | 8-16% 338 | 0.2-1% 343 | v.3 |
| D 318 | 0.42-1.2% 334 | 18-30% 339 | 0.13-2.7% 344 | v.4 |
| n 319 | n-thc% | n-cbd% | n-terpenoids% | v.n |

(51) Int. Cl.
    *A24B 7/00*      (2006.01)
    *A24B 15/16*      (2020.01)
    *A61K 36/185*      (2006.01)

(56) References Cited

U.S. PATENT DOCUMENTS

| | | | |
|---|---|---|---|
| 9,655,381 | B2 | 5/2017 | Sinclair, Jr. |
| 2009/0014017 | A1 | 1/2009 | Enslin |
| 2016/0366926 | A1 | 12/2016 | Uren |
| 2017/0188623 | A1* | 7/2017 | Cranford .................. A24C 5/06 |

OTHER PUBLICATIONS

Rnwy29erclr, "Re: Trimmin shears?", Jan. 18, 2010, 420 Magazine, accessed Nov. 9, 2017, https://www.420magazine.com/forums/harvest-preparation-and-curing/110690-trimming-shears.html.*

Ghaly, Sera Jane; "What is Kief and 6 great ways to use it", Jan. 7, 2016, Herb, accessed Nov. 9, 2017, https://herb.co/2016/01/07/kief-6-great-ways-use/.*

Casano, Salvatore & Grassi, Gianpaolo & Martini, V & Michelozzi, Marco. (2011). Variations in Terpene Profiles of Different Strains of *Cannabis sativa* L. Acta horticulturae. 925. 115-121. 10.17660/ActaHortic.2011.925.15. Accessed Nov. 9, 2017 https://www.researchgate.net/publication/235348187_Variations_in_Terpene_Profiles_of_Different_Strains_of_Cann.*

Bedrocan Canada, Inc., "Newly Licensed Medicinal Cannabis Producer, Bedrocan Canada, to Import Legal Cannabis Strains to Canada" Jan. 14, 2014, Marketwired.com (NASDAQ) accessed on Mar. 22, 2018 at: http://www.marketwired.com/press-release/newly-licensed-medicinal-cannabis-producer-bedrocan-canada-import-legal-cannabis-strains-1868795.htm.*

Canopy Growth Corporation, "Bedrocan Canada launches bedro-oils, Standardized Cannabis Oil Products" Jun. 20, 2016 CNW Group Ltd., accessed on Mar. 22, 2018 at https://www.newswire.ca/news-releases/bedrocan-canada-launches-bedro-oils-standardized-cannabis-oil-products-583603891.html.*

Sigma-Aldrich, "Cannabis Testing", Mar. 2017 (Year: 2017).*

PerkinElmer, "Cannabis Analysis", Jun. 30, 2015 (Year: 2015).*

Ruchlemer, et al., "Inhaled medicinal cannabis and the immunocompromised patient", Support Care Cancer, Sep. 13, 2014, Springer. (Year: 2014).*

* cited by examiner

DEVICE FOR DELIVERY OF SMOKABLE CANNABIS AND MANUFACTURING METHOD FOR SAME

CROSS-REFERENCE TO RELATED APPLICATIONS

None.

BACKGROUND OF THE INVENTION

Field of the Invention

The disclosure relates to the field of consumable cannabis delivery devices, and more particularly to a delivery device for smokable cannabis and a manufacturing method for same.

Discussion of the State of the Art

In the field of consumable cannabis, many states have passed legislation legalizing use of such cannabis for both medical and recreational usage. Pending legislation in additional states may greatly affect the current landscape of cannabis usage, as more people may be introduced to the use of cannabis either as a recreational endeavor or as a treatment for a plurality of medical issues and diseases. While the uses of medical cannabis and recreational cannabis appear to differ, there is a similarity in delivery of both medical and recreational cannabis to the consumer. Consumable cannabis; be it smoked, vaporized, or consumed in some other form, may not come from the same batch of cannabis or even the same manufacturing method, resulting in possible distinguishable differences between batches of consumable cannabis.

What is needed, is a means to provide a delivery device for a batch of smokable cannabis and to provide a manufacturing method for identical batches of smokable cannabis, so that any differences between batches are either nearly eliminated or nearly indistinguishable from one another.

SUMMARY OF THE INVENTION

Accordingly, the inventor has conceived and reduced to practice, in a preferred embodiment of the invention, a manufacturing method for consistent batches of consumable cannabis to be smoked in a delivery device (generally resembling a hollowed-out cylindrical-type shape; however, it should be appreciated that other final delivery device shapes may be used according to a desired arrangement or use case of the invention). Accordingly, in this manufacturing method, batches of flowers and leaves from one or more cultivars of cannabis, may be shredded and sterilized for an initial test to determine concentration of desired active compounds per batch sample. These batch samples may then be combined together(according to specific proportions as required for a targeted therapeutic outcome) to create a specific active compound profile, such that the finished product retains a desired potency effect that is consistent across multiple batches. Blended batches may be tested a second time for confirmation of correct active compound profiles; if a discrepancy occurs, blends may be reformulated and sent through testing procedures until desired profiles are reached. Once desired potency of active compound profiles are reached; the batch is manufactured into a smokable cannabis form, packaged and labeled, and finally distributed to consumers.

According to a preferred embodiment, a method for manufacturing smokable cannabis of a consistently defined active compound composition, has been devised and reduced to practice. This method comprises a plurality of cannabis plants and cannabis cultivars; cannabis cultivars contain concentrations of active compounds and are differentiated into two groups of cultivars: each first cannabis cultivar contains an active compound profile that differs from each second cannabis cultivar active compound profiles. This method also comprises a shredding device configured to reduce cannabis plant materials to a reproducible range of mesh dimensions, a mixing device configured to combine specific amounts of the reduced cannabis material from each plurality of cannabis cultivars, and a loading device configured to load a measured quantity of the combined cannabis material into a some-able delivery device. This method for manufacturing smokable cannabis with an active compound comprises the steps of: harvesting flowers and leaves from a plurality of cannabis plants and cannabis cultivars, shredding the flowers and leaves to a mesh size able to be loaded into a cylindrical delivery device, combining specific amounts of cannabis plant material from one or more cannabis strains to produce a batch sample with a specific active compound, and loading the batch sample into a cylindrical smokable device to be distributed to consumers for use.

Further, according to another preferred embodiment of the invention, a method for manufacturing a defined active compound profile has been developed and reduced to practice. Active cannabis compounds are chosen from a set of delta-9-tetrahydrocannabinol, cannabidiol, cannabichromene, cannabinol, cannabigerol, tetrahydrocannabivarin, cannabidivarin, delta-8-tetrahydrocannabinol, delta-9-tetrahydrocannabinol, and tetrahydrocannabinolic acid. Active cannabis compounds are chosen from a set comprising β-myrcene, α-pinene, ocimene, terpineol, β-caryophyllene, linalool, limonene, terpinolene, valencene, geraniol, phellandrene, carene, terpinene, fenchol, borneol, bisabolol, phytol, camphene, sabinene, camphor, isoborneol, menthol, cedrene, nerolidol, guaiol, isopulegol, geranyl, acetate, cymene, eucalyptol, and pulegone. A measured quantity of at least one exogenous active cannabis compound is added to at least one mixture of cannabis plant materials.

BRIEF DESCRIPTION OF THE DRAWING FIGURES

The accompanying drawings illustrate several embodiments of the invention and, together with the description, serve to explain the principles of the invention according to the embodiments. It will be appreciated by one skilled in the art that the particular embodiments illustrated in the drawings are merely exemplary, and are not to be considered as limiting of the scope of the invention or the claims herein in any way.

DETAILED DESCRIPTION

Figure 1:
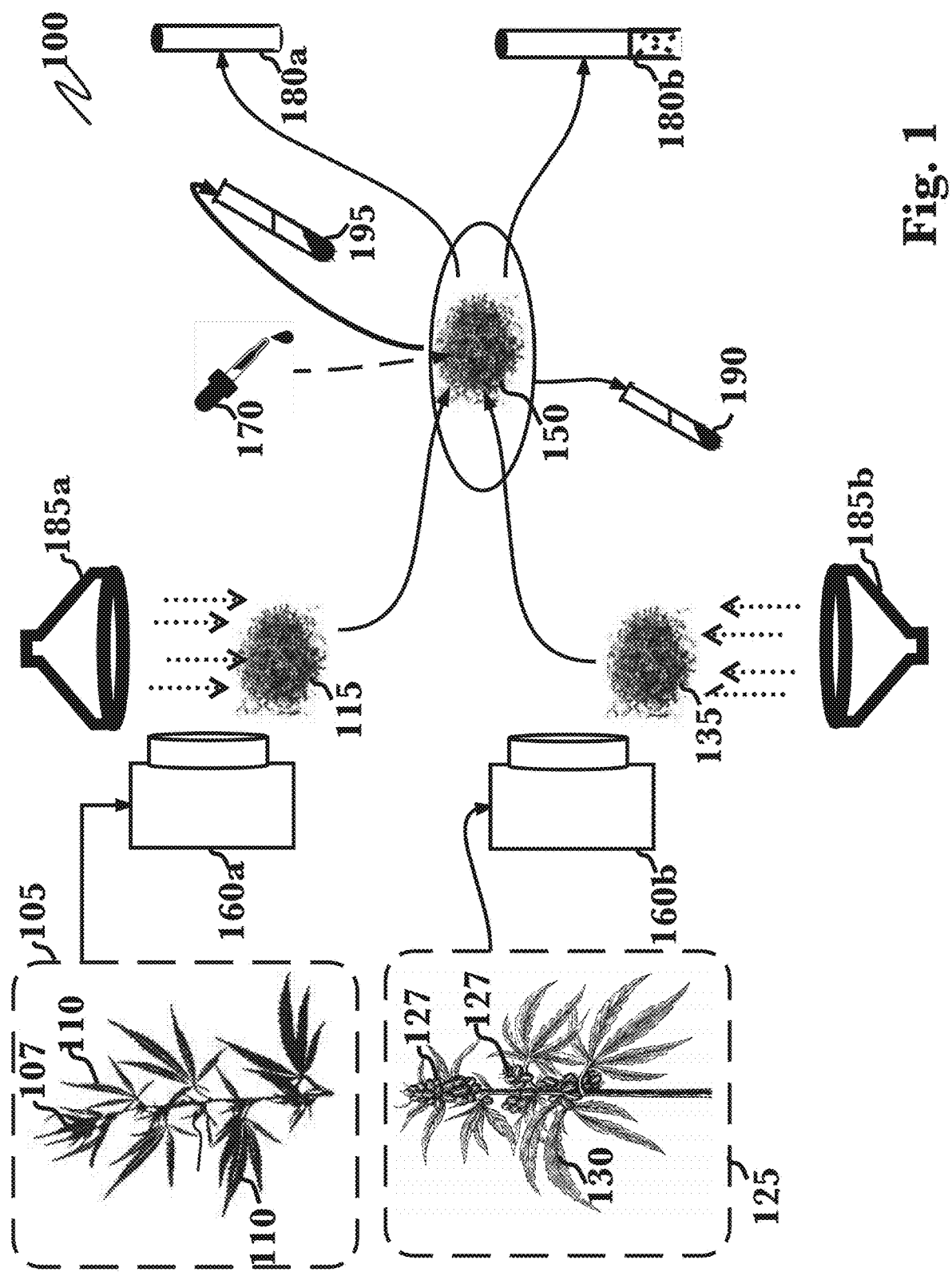
FIG. 1 is a diagram illustrating an exemplary method for manufacturing smokable cannabis with defined active compound composition, according to a preferred embodiment of the invention.

The inventor has conceived, and reduced to practice, a method for manufacturing smokable cannabis with a defined active compound composition and a smokable cannabis delivery device.

One or more different inventions may be described in the present application. Further, for one or more of the inventions described herein, numerous alternative embodiments may be described; it should be understood that these are presented for illustrative purposes only. The described embodiments are not intended to be limiting in any sense. One or more of the inventions may be widely applicable to numerous embodiments, as is readily apparent from the disclosure. In general, embodiments are described in sufficient detail to enable those skilled in the art to practice one or more of the inventions, and it is to be understood that other embodiments may be utilized and that structural, compound constituent, constituent compound ratio, constituent compound isomer, constituent compound concentration and other changes may be made without departing from the scope of the particular inventions. When an active compound with multiple isomers is cited, it is to be understood that a mixture containing equal concentrations of those isomers is in use unless otherwise specified. Accordingly, those skilled in the art will recognize that one or more of the inventions may be practiced with various modifications and alterations. Particular features of one or more of the inventions may be described with reference to one or more particular embodiments or figures that form a part of the present disclosure, and in which are shown, by way of illustration, specific embodiments of one or more of the inventions. It should be understood, however, that such features are not limited to usage in the one or more particular embodiments or figures with reference to which they are described. The present disclosure is neither a literal description of all embodiments of one or more of the inventions nor a listing of features of one or more of the inventions that must be present in all embodiments.

Headings of sections provided in this patent application and the title of this patent application are for convenience only, and are not to be taken as limiting the disclosure in any way.

When a single device or article is described, it will be readily apparent that more than one device or article may be used in place of a single device or article. Similarly, where more than one device or article is described, it will be readily apparent that a single device or article may be used in place of the more than one device or article.

Techniques and mechanisms described or referenced herein will sometimes be described in singular form for clarity. However, it should be noted that particular embodiments include multiple iterations of a technique or multiple manifestations of a mechanism unless noted otherwise. Process descriptions or blocks in figures should be understood as representing modules, or segments which include one or more executable actions for implementing specific functions or steps in the process. Alternate implementations are included within the scope of embodiments of the present invention in which, for example, functions may be executed out of order from that shown or discussed, including substantially concurrently or in reverse order, depending on the functionality involved, as would be understood by those having ordinary skill in the art.

Detailed Description of Exemplary Embodiments

While strictly illegal in all states until recently, cannabis, more commonly known as marijuana since the mid-1930s, has been extensively cultivated throughout the world for centuries and secretly cultivated within the United States and elsewhere where the plant and its products are illegal to the point where there are tens if not hundreds of cultivars or strains which comprise differing levels of the many active compounds that give cannabis its wide range of sought after effects. A family of active compounds that are specific to cannabis and its close relative plant species is the cannabinoids of which nearly 70 have been identified that have overlapping but different effect profiles. Perhaps best known and present at high but varying concentration in cannabis strains are delta-9-tetrahydrocannabinol (THC) which may vary from approximately 27% to as low as 0.1% (wt/total isolate wt. Steep Hill Labs/steephill.com) depending on the cannabis strain and which is the psychoactive agent responsible for cannabis' ability to alter mood, to give the impression of altered consciousness and to cause feelings of euphoria which people consider the "cannabis high." Another cannabinoid, cannabidiol (CBD) may vary depending on the strain from approximately 30% to as low as 0.02% and to which the calming, contentment, "stoned feeling" effects of certain cannabis strains is attributed. A third major cannabinoid, cannabinol (CBN) is found in stored, dried cannabis and may also be a thermal breakdown product of THC. CBN is therefore usually found in higher concentrations in smoke or vaporization delivery methods. It is strongly sedative and again may add the "stoned," inactive, reputation of some cannabis users. A second family of active compounds, the terpenes, are a very large family of aromatic branched hydrocarbons that are produced by a wide variety of plant species and are among the active ingredients of essential oils created from them. Different cannabis strains produce widely different terpenes and their derivative terpenoids at widely different levels that may range from 0% to 5% wt/wt and which may give different cannabis strains their unique odors. Some of the Terpenes' impact on cannabis effects include potentiating the effects of specific cannabinoids such as THC and having weak sedative, anti-anxiety and pain-reducing properties of their own.

It is the differences in the levels and types of both cannabinoids and terpenes, as well as the presence of less-prevalent compounds such as flavonoids, that imbue cannabis strains with a wide range of medically and recreationally desirable effects. Accordingly, various aspects of the invention described herein assay and blend cannabis raw material to control the in toto effects of each identically-typed smokable device in a set and the in toto effects of identically-typed smokable devices between batches.

Cannabinoids, terpenes and flavonoids employed in aspects are to be assumed isolated and purified by previously-published means best suited for that active compound, which may include (but are not limited to) column chromatography, gas chromatography, supercritical fluid extraction, either with or without additional, modifying solvents, as well as other methods known to those skilled in the art.

When single cannabinoids, multiple cannabinoid mixtures, cannabinoid-terpene mixtures, cannabinoid-terpene-flavonoid mixtures, terpene, multiple terpene mixtures, and terpene-flavonoid mixtures are listed in aspects, are to be assumed administered by methods previously cited to both retain the stability of all active compounds cited in a formulation and to deliver all active compounds within the formulation in a manner of optimal bioavailability and bioactivity of each active compound. These delivery methods may comprise, but are not limited to smoking cannabis biomatter infused with a known amount of the formulation, inhalation of vapor comprising the formulation, and administration of sublingual tinctures of the formulation as well as other administrative methods known to be applicable to those with ordinary skill in the art.

It will be readily apparent that more than one method of active compound assay may be used for assay of a single formulation cited in an aspect and that any method of assay that maintains both constituent active compound stability and high bioavailability of each active compound while maintaining relevance to concentrations expected present within the intended method of administration, smoking, may be employed for a cited formulation.

Conceptual Architecture

FIG. 1 is a diagram illustrating an exemplary method for manufacturing smokable cannabis with defined active compound composition 100, according to a preferred embodiment of the invention. Desired aspects of the invention may originate with harvested parts of one or more cannabis strains or cultivars 105, 125. Each cultivar is expected to produce a significant level of one or more active cannabis compounds such as but not limited to: δ-9-tetrahydrocannabinol (THC), cannabidiol (CBD), cannabichromene (CBC), β-myrcene, and menthol, as well as potentially a number of other active compounds found in cannabis. From cultivars 105, 125; flowers 107, 127 and leaves 110, 130 may be primary targets for harvesting although other parts (such as stems or roots) of cultivars 105, 125 may also be harvested if desired for manufacturing. Harvested material is shredded 160a, 160b by manual shredding methods and/or mechanical shredding methods, to a mesh size ranging from 2 millimeters (mm) to 5 mm for width and a mesh size ranging from 5 mm to 15 mm for length, of shredded plant material 115, 135. Any plant material 115, 135 that is undesirable, such as stems or stem fragments, or plant remnants that are too small for inclusion, may be removed after shredding process 160a, 160b. Plant material 115, 135 may now be sterilized by radiation 185a, 185b (it should be appreciated that sterilization methods such as, but not limited to, ultraviolet radiation or heat over an extended time period may be used, according to a desired use case of the invention) or in a solution of water and 1-10% hydrogen peroxide for 15 to 90 minutes. Sterilization 185a, 185b of plant material 115, 135 should not reduce potency of target active cannabis compounds, but should eliminate undesirable microbial contaminants; it should also be appreciated that, depending on sterilization method used, some active cannabis compounds may be activated during the sterilization process if these compounds are found in material and are desired in the final product.

Plant material 115, 135 from cultivars 105, 125 may then be combined into calculated ratio-based batches 150 of material to achieve target concentrations of specific active cannabis compounds based upon component make-up of cultivars 105, 125. In the instance where desired active cannabis compounds and/or desired concentration of active cannabis compounds are not found, a pre-existing solution 170 of desired and purified active compound composed of a known concentration may be added to material batches 150 prior to analysis 195. Detailed composition of active compounds within material batches 150 may be identified using analysis 195 methods of isolation and assay. Material batches 150 may also be analyzed for microbial contamination within acceptable standards 190. Once passing all analyses 190, 195, material batches 150 may be manually or mechanically loaded into a hollowed-out cylindrical-type shape delivery device 180a, 180b composed of hemp paper or other substance (it should be appreciated that other devices may be used such as but not limited to; devices composed of plastic or metal, devices comprising filters or tipping paper, or other devices known to those skilled in the art according to a desired use basis of the invention). Once material batches 150 are loaded into delivery device 180a, 180b, devices 180a, 180b are then toasted from 180° F. to 220° F. for 3 to 15 minutes. Finished product may then be labeled, packaged, and distributed.

Figure 2:
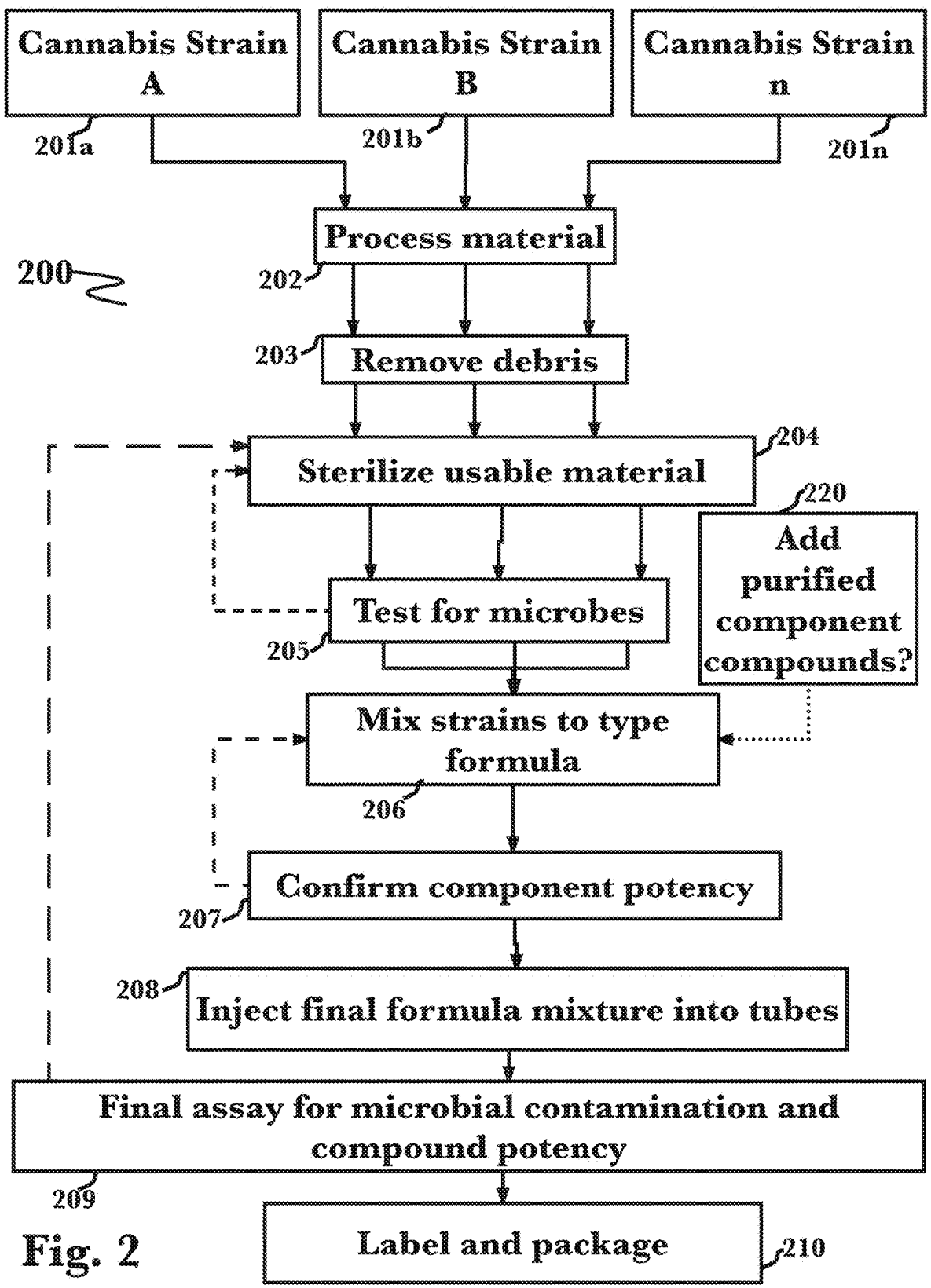
FIG. 2 is an exemplary method diagram illustrating a generalized method for manufacturing smokable cannabis with defined active compound composition, according to a preferred embodiment of the invention.

FIG. 2 is an exemplary method diagram illustrating a generalized method for manufacturing smokable cannabis with defined active compound composition 200, according to a preferred embodiment of the invention. One or more cannabis cultivars may be selected for harvesting material based upon known active cannabis compounds found in cultivar strains 201a, 201b, 201n. This material is processed 202 by harvesting form cultivars, drying plant materials, and shredding to a size range of 5 mm to 15 mm length and 2 mm to 5 mm width. Undesirable parts such as stems and stem fragments may be discarded 203. Material is then sterilized 204 by heat, ultraviolet radiation, or other sterilization methods, and samples tested 205 for efficacy of sterilization. Plant materials from multiple cultivar strains 201a, 201b, 201n may be mixed together 206 to create material batches with desired active cannabis compound profiles. In cases where desired compound profiles are not achieved, pre-existing solutions of purified active cannabis compound concentrations 220 may be added to batches. Active compound levels within each batch may be assayed (analyzed) 207 prior to being loaded into delivery devices 208. Batch samples may be analyzed again for compound potency and for microbial contamination 209. Finished product may then be toasted, labeled, packaged, and sent for distribution 210 to consumers.

Figure 3:
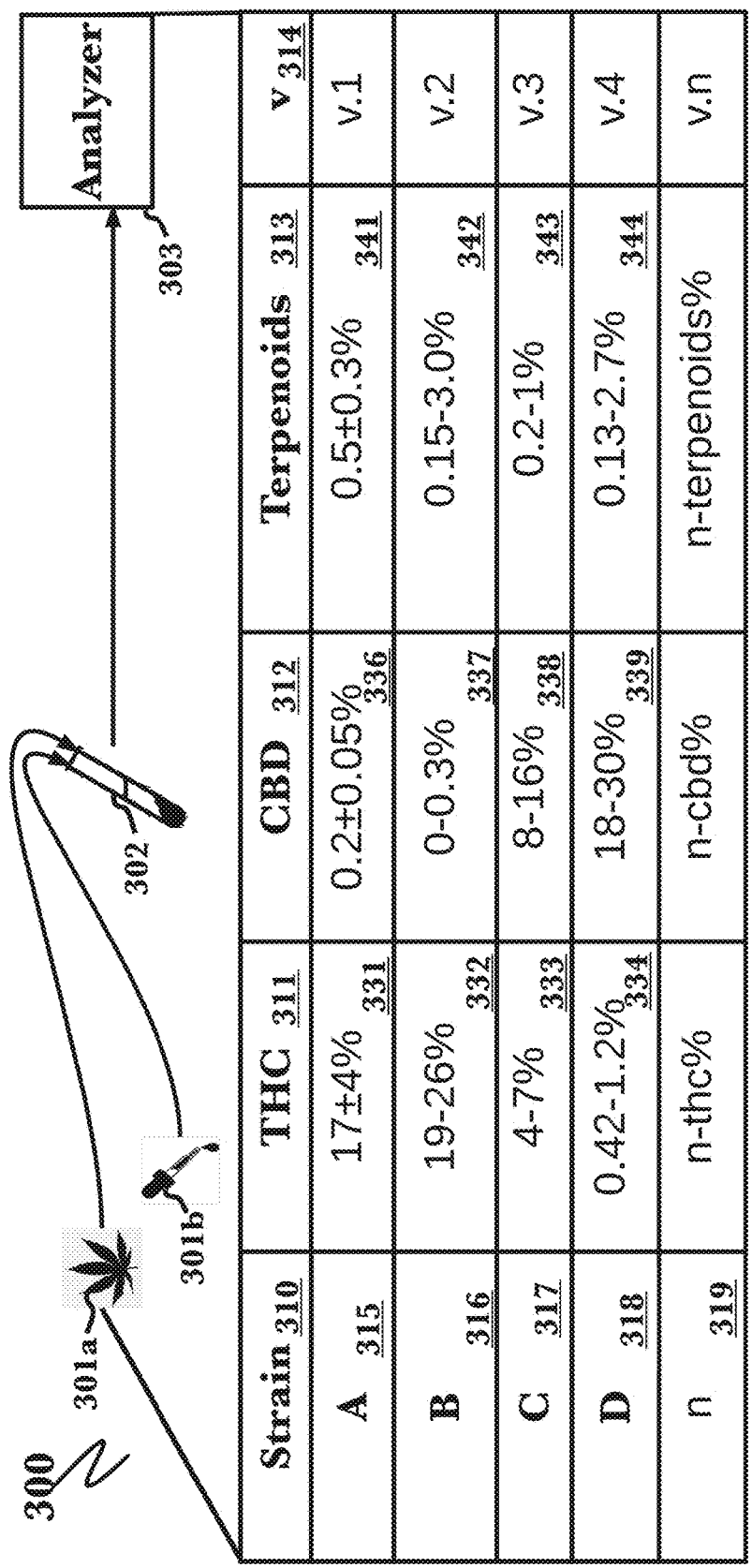
FIG. 3 is an exemplary table diagram illustrating an analysis of active compound make-up of multiple hypothetical cannabis strains, according to a preferred embodiment of the invention.

FIG. 3 is an exemplary table diagram illustrating an analysis of active compound make-up of multiple hypothetical cannabis strains 300, according to a preferred embodiment of the invention. Different cannabis strains may express differing levels of desired compounds and compound potency. Table 300 denotes a small number of possible active compounds and amounts of each listed compound, expressed as a percent weight compound/total weight extracted material (% $wt_{compound}$/$wt_{totalExtract}$[% $wt_a$/$wt_t$]). Active compound liberation such as from; smoked, dried, or vaporized buds 301a, or kief, hash, or tincture 301b, may change active compound levels and ratios due to processing mechanics. Given these possible changes, liberation methods should be independently tested 302 for analysis accuracy 303. Table is set up into columns of cannabis strains 310, and active compounds found within strains; delta-9-tetrahydrocannabinol (THC) 311, cannabinoids (CBD) 312, terpenoids 313, and 314 represents any additional compounds that can be tested for. Column 310 lists a plurality of hypothetical cannabis strains; strain A 315, strain B 316, strain C 317, strain D 318, and strain n 319. Columns 311, 312, 313, and 314, list active cannabis compounds that may be found in each strain of column 310. All active compound levels are listed in $wt_{compound}$/$wt_{totalExtract}$ some as mean±variance 331, 336, 341 while other compounds 332, 333, 334, 337, 338, 339, 341, 342, 343, 344 are listed as ranges. Levels may vary widely between strains; THC 311 levels may vary from 26% 332 for strain B 316 while strain D 318 may have levels at 0.42% 334. CBD 312 levels could vary from 30% 339 in strain D 318 to an unmeasurable level 337 in strain B 316. The terpenoids 313, which are a large family of related compounds, follow similar variability between strains. Please note that this figure is presented solely to effectively illustrate that large differences may exist between strains in the levels of active cannabis compounds. As the total level of a single active compound and the combination of the levels of two or more active compounds may affect the cannabis experience, illustration of a small number of compounds was necessary to make several salient points. The small number of strains and compounds as well as the combination of all terpenoids into one column was to produce a clear basis for disclosure and does not in any way reflect the function of the embodiments.

Figure 4:
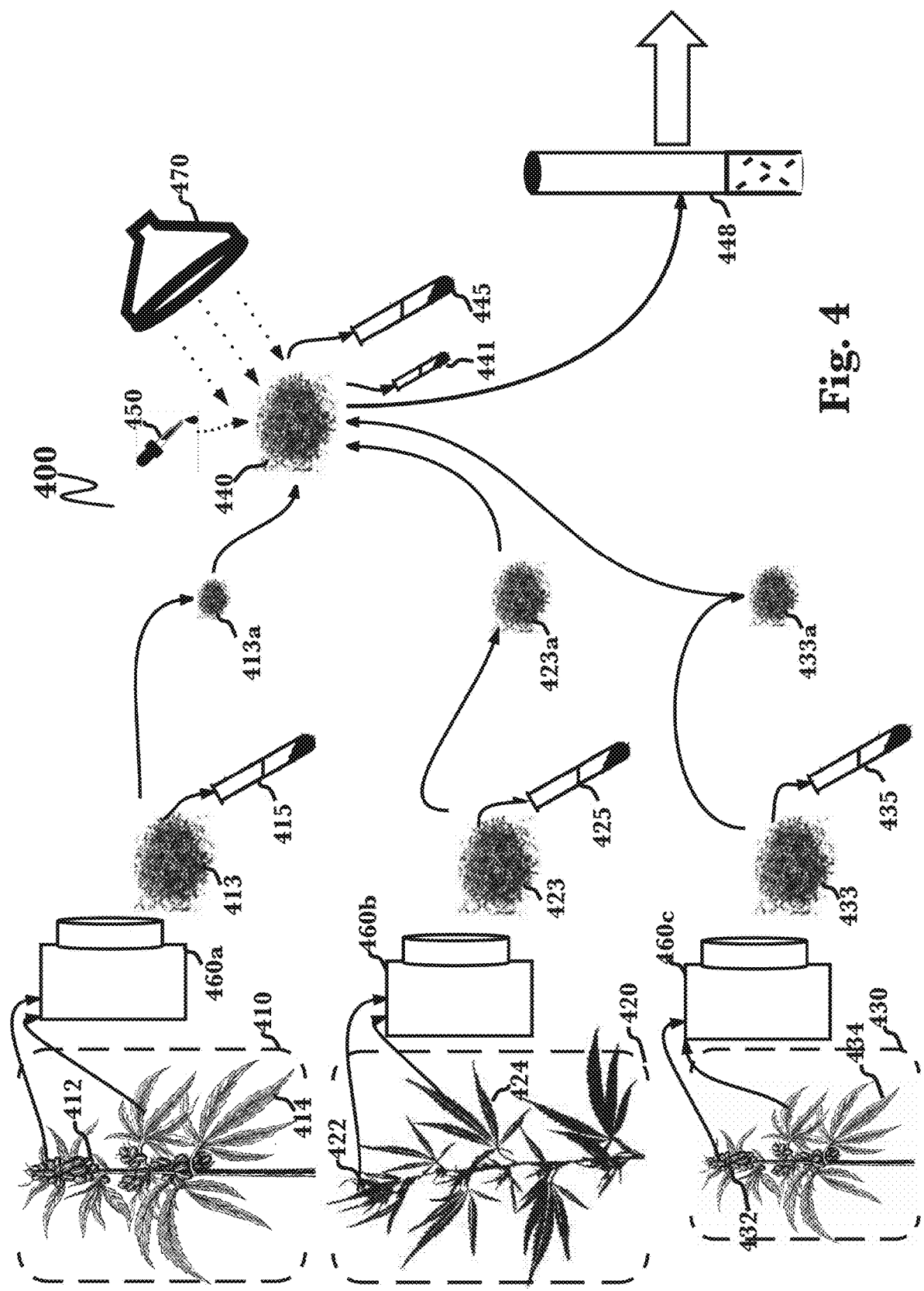
FIG. 4 is an exemplary diagram illustrating a method to confirm that labeled smokable cannabis delivery devices comprise the cannabis active compound profile of their intended type.

FIG. 4 is an exemplary diagram illustrating a method to confirm that labeled smokable cannabis delivery devices comprise the cannabis active compound profile of their intended type 400. One or more cannabis cultivars 410, 420, 430 may express differing profiles of active cannabis compounds such as but not limited to; δ-9-tetrahydrocannabinol (THC), cannabidiol (CBD), cannabichromene (CBC), beta-myrcene, and menthol among a plurality of other active cannabis compounds. Flowers 412, 422, 432 and leaves 414, 424, 434 may be harvested from cultivars 410, 420, 430 and harvested material is then shredded manually 460a, mechanically 460b, or by a combination of both methods 460c. Sizes may range from 2 mm to 5 mm in width and 5 mm to 15 mm in length, as a means for finished product to fit inside smokable delivery device 448. Each batch of material 413, 423, 433 may be assayed 415, 425, 435 for active cannabis compound profiles to confirm potency. Calculated ratios 413a, 423a, 433a of plant material 413, 423, 433 are then mixed into a single material batch 440 for desired active cannabis compound profile. If batch 440 fails to produce desired active compound profile, pre-existing exogenous solutions composed of desired active compound concentrations 450 may be added to material batch 440. Material batch 440 may then be sterilized 470 by methods such as radiation, ultraviolet irradiation, or heat over extended periods of time, or by other sterilization methods known to those skilled in the art. Material batch 440 is then tested for residual microbial contamination 441 and analyzed to confirm formulated batches 440 active cannabis compound potency 445. In cases of insufficient potency, batch material 413, 423, 433 may be reformulated 413a, 423a, 433a, into a new batch 440 and retested 450, 470, 441, 445 until desired potency standard is met. Standard compliant batches 440 are then loaded into a cylindrical-type delivery device 448, toasted between 180° F. to 220° F. for 3 to 15 minutes, labeled, packaged, and sent for distribution to consumers.

In various embodiments, functionality for implementing systems or methods of the present invention may be distributed among any number of manufacture stations or devices. For example, various harvesting devices, processing devices, such as shredders, tube loaders and packagers may be employed for performing various functions in connection with the present invention, and such modules may be variously implemented within a configuration which combines multiple functions or performs each function within distinct components.

The skilled person will be aware of a range of possible modifications of the various embodiments described above. Accordingly, the present invention is defined by the claims and their equivalents.

What is claimed is:

1. A method for manufacture of smokable cannabis device of defined active compound composition comprising the steps of:
   a) harvesting flowers and leaves from a plurality of cannabis plants from a plurality of cannabis strains each expressing a different active cannabis compound profile using shears;
   b) for each of the plurality of cannabis strains, shredding the flowers and leaves from the plurality of cannabis plants to produce a reproducible mesh size of between 2 millimeters and 5 millimeters in width and 5 millimeters and 15 millimeters in length of cannabis plant material able to be loaded into a cylindrical smokable tube using a shredding device;
   c) assaying the shredded cannabis plant material to confirm the active cannabis compound profile in each of the plurality of cannabis strains;
   d) combining specific amounts of the shredded cannabis plant material from at least two of the plurality of cannabis strains to produce a cannabis plant material mixture possessing a specific active cannabis compound profile using a mixing device,
   e) sterilizing the mixture of cannabis plant material;
   f) analyzing the mixture of cannabis plant material for residual microbial contamination and to confirm that the specific active cannabis compound profile is present;
   g) loading the mixture of cannabis plant material into the cylindrical smokable tube using a loading device; and
   h) toasting the cylindrical smokable tube at between 180 and 220 degrees Fahrenheit for between 3 and 15 minutes prior to packaging the tube as a finished product;
   wherein the specific amounts of each cannabis strain used to produce the cannabis plant material mixture is based at least in part on the results of the analysis of the shredded cannabis plant material from each strain.

2. The method of claim 1, wherein the active cannabis compounds are chosen from a set comprising delta-9-tetrahydrocannabinol, cannabidiol, cannabichromene, cannabinol, cannabigerol, tetrahydrocannabivarin, cannabidivarin, delta-8-tetrahydrocannabinol, delta-9-tetrahydrocannabinolic acid, and cannabidiolic acid.

3. The method of claim 1, wherein the active cannabis compounds are chosen from a set comprising myrcene, α pinene, ocimene, terpineol, beta-caryophyllene, linalool, limonene, terpinolene, valencene, geraniol, phellandrene, carene, terpinene, fenchol, borneol, bisabolol, phytol, camphene, sabinene, camphor, isoborneol, menthol, cedrene, nerolidol, guaiol, isopulegol, geranyl, cymene, and eucalyptol.

4. The method of claim 1, further comprising the steps of adding a measured quantity of at least one exogenous active cannabis compound the mixture of cannabis plant material and retesting the mixture to achieve a desired potency standard prior to loading the mixture into the cylindrical smokable tube.

* * * * *